(12) United States Patent
Weinkauff et al.

(10) Patent No.: US 6,320,071 B1
(45) Date of Patent: Nov. 20, 2001

(54) PRODUCTION OF 2-CARBOXYALKYL (PHENYL)PHOSPHINIC ACID

(75) Inventors: David J. Weinkauff, Manchester; Frank E. Paulik, St. Louis, both of MO (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/505,833

(22) Filed: Feb. 17, 2000

Related U.S. Application Data

(60) Provisional application No. 60/120,991, filed on Feb. 19, 1999.

(51) Int. Cl.⁷ ........................................................ C07F 9/22
(52) U.S. Cl. ................................................................ 562/24
(58) Field of Search ................................................. 562/24

(56) References Cited

U.S. PATENT DOCUMENTS

| | | | |
|---|---|---|---|
| 4,081,463 | 3/1978 | Birum, et al. | 260/502.4 R |
| 4,769,182 | 9/1988 | Hazen | 260/502.4 R |
| 5,334,760 | 8/1994 | Wachi, et al. | 562/817 |

*Primary Examiner*—Joseph K. McKane
*Assistant Examiner*—Joseph Murray
(74) *Attorney, Agent, or Firm*—Lathrop & Gage L.C.

(57) ABSTRACT

Processes for producing 2-carboxyalkyl(phenyl)phosphinic acid comprising hydrolyzing the reaction mixture produced from the reaction of dichloro(phenyl)phosphine with a carboxylic acid in the presence of water, wherein the hydrolysis is conducted with reduced levels of water.

17 Claims, 2 Drawing Sheets

□ 16.5:1
× 4.1:1
△ 7.4:1

□ 16.5:1
× 4.1:1
△ 7.4:1

PRODUCTION OF 2-CARBOXYALKYL (PHENYL)PHOSPHINIC ACID

CROSS-REFERENCE TO RELATED APPLICATIONS

This application claims the benefit of priority under 35 U.S.C. §119(e) of U.S. Provisional Patent Application No. 60/120,991, filed Feb. 19, 1999.

STATEMENT REGARDING FEDERALLY SPONSORED RESEARCH OR DEVELOPMENT (NOT APPLICABLE)

BACKGROUND OF THE INVENTION

This invention relates to a process for preparing 2-carboxyalkyl(phenyl)-phosphinic acid. In a specific aspect, this invention relates to an improved hydrolysis process. In a more specific aspect, this invention relates to a process for preparing 2-carboxyethyl(phenyl)-phosphinic acid using an improved hydrolysis process.

2-Carboxyethyl(phenyl)phosphinic acid, a flame retardant additive for polymers such as polyesters, has been prepared by first reacting acrylic acid with dichloro(phenyl)phosphine. This reaction mixture was then subjected to a separate hydrolysis step to obtain the 2-carboxyethyl(phenyl)phosphinic acid.

U.S. Pat. No. 4,081,463 (Birum et al.) discloses a process in which a 25–45% molar excess of acrylic acid was used in the reaction of acrylic acid with dichloro(phenyl)phosphine. For the hydrolysis step, the '463 patent discloses adding the undiluted reaction product of acrylic acid and dichloro(phenyl)phosphine to at least enough water to complete hydrolysis, with it being advantageous to use a significant excess of water to aid stirring and temperature control. In fact, use of a 5 to 15 molar excess of water is taught as being convenient. This molar excess of water is equivalent to conducting the hydrolysis using 12 to 32 moles water per mole of dichloro(phenyl)phosphine charged to the reaction of acrylic acid with dichloro(phenyl)phosphine. Conducting the hydrolysis in this manner produces 2-carboxyethyl(phenyl)phosphinic acid as a fine white solid.

U.S. Pat. No. 4,769,182 (Hazen) discloses a process in which a 0–20% molar excess of acrylic acid was used in the reaction of acrylic acid with dichloro(phenyl)phosphine. For the hydrolysis step, the '182 patent discloses that typical hydrolysis conditions for acid chlorides and similar water-reactive species are used, with a "drowning" technique being preferred. The drowning technique involves the use of significant excess water, i.e. 25.7 moles water per mole of dichloro(phenyl)phosphine charged to the reaction of acrylic acid with dichloro(phenyl)phosphine. Conducting the hydrolysis in this manner produces 2-carboxyethyl(phenyl)phosphinic acid as a white microcrystalline powder.

It is desirable to produce 2-carboxyalkyl(phenyl)phosphinic acid with improved product recovery and washing resulting in improved product quality.

It has now been surprisingly discovered that conducting the hydrolysis with significantly less water present than suggested by the prior art produces 2-carboxyalkyl(phenyl)phosphinic acid having better filterability than obtained using the prior art processes.

BRIEF SUMMARY OF THE INVENTION

It is an object of the invention to provide a process for producing 2-carboxyalkyl(phenyl)phosphinic acid having improved filterability. It is a further object of the invention to produce 2-carboxyalkyl(phenyl)phosphinic acid having improved purity. It is a still further object of the invention to provide a process for producing 2-carboxyalkyl(phenyl) phosphinic acid which results in improved product washing and faster filtration. It is yet a further object of the invention to provide a process for producing 2-carboxyalkyl(phenyl) phosphinic acid which enables HCl produced during the hydrolysis reaction to be removed prior to recovery of the 2-carboxyalkyl(phenyl)phosphinic acid from the hydrolysis reaction mixture.

According to the invention, a process for producing 2-carboxyalkyl(phenyl)phosphinic acid is provided which comprises (a) admixing water and a first reaction mixture comprising the products of the reaction of dichloro(phenyl)phosphine and a carboxylic acid selected from acrylic acid or methacrylic acid, and (b) hydrolyzing the reaction products of the first reaction mixture to produce a second reaction mixture comprising 2-carboxyalkyl(phenyl)phosphinic acid; wherein the amount of water admixed with the first reaction mixture in step (a) is about 2 to about 7.5 moles water per mole of dichloro(phenyl)phosphine charged to the reaction between dichloro(phenyl)phosphine and carboxylic acid.

Further according to the invention, a process for producing 2-carboxyalkyl(phenyl)phosphinic acid is provided which comprises (a) admixing water and a first reaction mixture comprising the products of the reaction of dichloro (phenyl)phosphine and a carboxylic acid selected from acrylic acid or methacrylic acid, and (b) hydrolyzing the reaction products of the first reaction mixture to produce a second reaction mixture comprising 2-carboxyalkyl(phenyl) phosphinic acid, and simultaneously removing at least a portion of the HCl present during the hydrolysis reaction; wherein the amount of water admixed with the first reaction mixture in step (a) is the amount effective to enable removal of at least about 20% of the theoretically available chlorine in the first reaction mixture during the hydrolysis.

DETAILED DESCRIPTION OF THE INVENTION

Figure 1:
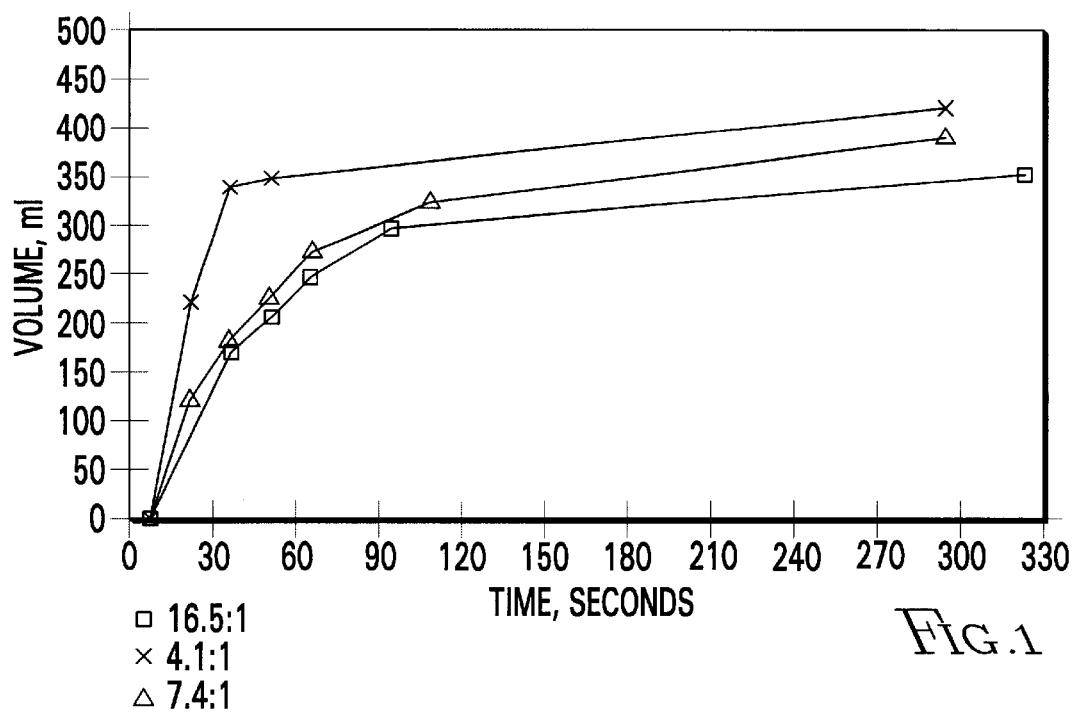
FIG. 1 is a plot of the mother liquor filtration rate at 14 psig filtration pressure.

A first embodiment of the invention relates to a process for producing a 2-carboxyalkyl(phenyl)phosphinic acid comprising (a) admixing water and a first reaction mixture comprising the products of the reaction of dichloro(phenyl) phosphine and a carboxylic acid selected from acrylic acid or methacrylic acid, and (b) hydrolyzing the reaction products of the first reaction mixture to produce a second reaction mixture comprising 2-carboxyalkyl(phenyl)phosphinic acid; wherein the amount of water admixed with the first reaction mixture in step (a) is about 2 to about 7.5 moles water per mole of dichloro(phenyl)phosphine charged to the reaction between dichloro(phenyl)phosphine and carboxylic acid.

The 2-carboxyalkyl(phenyl)phosphinic acid produced according to the processes of the invention depends on the carboxylic acid used. When acrylic acid is used, the 2-carboxyalkyl(phenyl)phosphinic acid is 2-carboxyethyl (phenyl)phosphinic acid (I), also known as 3-(hydroxyphenyl-phosphinyl)propanoic acid or 3-HPP.

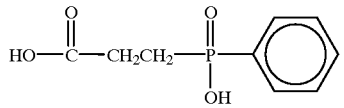

(I)

When methacrylic acid is used, the 2-carboxyalkyl(phenyl) phosphinic acid is 2-carboxy-propyl(phenyl)phosphinic acid (II), also known as 3-(hydroxyphenyl-phosphinyl)-2-methylpropanoic acid).

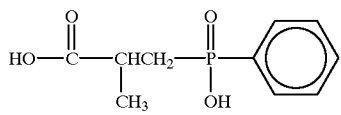

(II)

The currently preferred carboxylic acid is acrylic acid as the preferred 2-carboxyalkyl(phenyl)phosphinic acid is 2-carboxyethyl(phenyl)-phosphinic acid.

The reaction of dichloro(phenyl)phosphine, which is also known as phenylphosphonous dichloride or BPD, with carboxylic acid to produce the first reaction mixture can be run with stoichiometric amounts of the two reactants or with an excess of carboxylic acid typically up to about 45% molar excess. For example, when the carboxylic acid is acrylic acid, an excess of acrylic acid can be used such as disclosed in U.S. Pat. Nos. 4,081,463 and 4,769,182, which are both incorporated herein by reference. It is currently preferred to conduct this reaction in the presence of about 10 to about 20% molar excess of carboxylic acid.

When acrylic acid is used, the first reaction mixture comprises one or more compounds selected from 3-(chlorophenylphosphinyl)propionyl chloride, the cyclic anhydride of 2-carboxyethyl(phenyl)-phosphinic acid, and the mixed anhydride of acrylic acid with 3-chlorocarbonylethyl(phenyl)phosphinic acid, as disclosed in U.S. Pat. No. 4,081,463. The first reaction mixture may also contain minor amounts of other derivatives of acrylic acid including, but not limited to, 3-chloropropionic acid which is formed by the reaction of acrylic acid with HCl.

When methacrylic acid is used, the first reaction mixture comprises one or more compounds selected from 3-(chlorophenylphosphinyl)-2-methylpropionyl chloride, the cyclic anhydride of 2-carboxypropyl(phenyl)phosphinic acid, and the mixed anhydride of methacrylic acid with 3-chlorocarbonyl-2-methylethyl(phenyl)phosphinic acid. The first reaction mixture may also contain minor amounts of other derivatives of methacrylic acid including, but not limited to, 3-chloro-2-methyl propionic acid which is formed by the reaction of methacrylic acid with HCl.

The amount of water admixed with the first reaction mixture for the hydrolysis reaction is about 2 to about 7.5, preferably about 2 to about 6, and more preferably 2 to about 4.5, moles water per mole of dichloro(phenyl)phosphine charged to the reaction between dichloro(phenyl)phosphine and carboxylic acid. Generally, the water and the first reaction mixture are admixed by adding the first reaction mixture to the desired amount of water.

When the hydrolysis reaction is conducted with the water levels of the instant invention, HCl that is generated during the hydrolysis reaction or that is present in the first reaction mixture can be removed from the second reaction mixture as hydrolysis proceeds. The amount of HCl capable of being removed will be dependent on the amount of water added to the first reaction mixture for conducting the hydrolysis. Preferably, all of the HCl that is capable of being removed is removed during the hydrolysis reaction. In addition, 3-chloropropionic acid or 3-chloro-2-methyl propionic acid (depending on the specific carboxylic acid used) may also be removed with the HCl during hydrolysis.

A second embodiment of the invention relates to a process for producing 2-carboxyalkyl(phenyl)phosphinic acid comprising (a) admixing water and a first reaction mixture comprising the products of the reaction of dichloro(phenyl) phosphine and a carboxylic acid selected from acrylic acid or methacrylic acid, and (b) hydrolyzing the reaction products of the first reaction mixture to produce a second reaction mixture comprising 2-carboxyalkyl-(phenyl)phosphinic acid, and simultaneously removing at least a portion of the HCl present during the hydrolysis reaction; wherein the amount of water admixed with the first reaction mixture in step (a) is the amount effective to enable removal of at least about 20% of the theoretically available chlorine in the first reaction mixture during the hydrolysis.

The amount of water admixed with the first reaction mixture in step (a) is the amount effective to enable removal of at least about 20%, preferably at least about 35%, and more preferably at least about 50%, of the theoretically available chlorine in said first reaction mixture during the hydrolysis. Generally, the water and the first reaction mixture are admixed by adding the first reaction mixture to the desired amount of water.

During the hydrolysis reaction of the processes of the invention, it is preferred that essentially all of the HCl that is available for removal is removed from the reaction vessel used for conducting the hydrolysis reaction. The HCl that is removed can be recovered for further use or sale.

The temperature required in the hydrolysis reaction of the processes of the invention depends on the amount of water added to the first reaction mixture, i.e. amount of water present during hydrolysis. Generally, the lower the level of water the higher the hydrolysis temperature. Typically, the hydrolysis temperature will be about 60° C. to about 150° C., preferably about 85° C. to about 130° C.

The hydrolysis reaction can be conducted under suitable pressures ranging from vacuum to greater than atmospheric pressure. It is currently preferred to conduct the hydrolysis reaction at or near atmospheric pressure due to excellent results obtained under those conditions.

Further according to the processes of the invention, once the hydrolysis reaction has been completed additional water is added to the second reaction mixture to produce a diluted second reaction mixture. During addition of the additional water, the temperature of the reactor contents are maintained above the crystallization temperature.

The crystallization of the 2-carboxyalkyl(phenyl) phosphinic acid is conducted using conventional crystallization techniques. Typically, the temperature of the diluted second reaction mixture is cooled slowly, e.g. at 0.2° C. per minute, until crystallization has essentially been completed. At that point, the cooling rate can be increased and the diluted second reaction mixture cooled to the temperature at which recovery of 2-carboxyalkyl(phenyl)phosphinic acid is conducted.

Following crystallization, the 2-carboxyalkyl(phenyl) phosphinic acid is recovered by filtration or other conventional solids separation techniques. The solids are then washed and dried. The mother liquor or wash liquors obtained during filtration and washing can be recycled for use in the hydrolysis.

The processes of the invention produce 2-carboxyalkyl (phenyl)phosphinic acid having improved filterability than the prior art processes where hydrolysis is conducted with higher levels of water and crystallization is conducted with higher levels of HCl and 3-chloropropionic acid or 3-chloro-2-methyl propionic acid in the crystallization liquors. The improved filterability is advantageous in that it results in more efficient product washing and faster filtration. The removal of HCl according to the processes of the invention reduces the waste disposal costs and the recovered 2-carboxyalkyl(phenyl)phosphinic acid has higher purity, e.g. lower chloride content in the final product. This removal of the HCl produced during the reaction has an added advantage in that it provides for use of cheaper alloys in the downstream operations of filtration and drying.

EXAMPLES

Example 1

Dichlorophenylphosphine, 1808.4 g. (10.1 moles), was placed in a reactor under a nitrogen purge, stirred and warmed to 70° C. At temperature, dropwise addition of acrylic acid, 837.3 g. (11.62 moles), was started and the temperature was maintained at 80–85° C. during the addition. When the addition was complete, the mixture was maintained briefly at 80–85° C. and then heated further to 125–130° C. The mixture was maintained at 125–130° C. for one hour and then cooled to ambient temperature. This acrylation intermediates mixture was used as the feedstock for examples 2–8.

The following examples are based on preparing a 35% final slurry concentration of 2-carboxyethyl(phenyl) phosphinic acid after hydrolysis. Higher or lower final slurry concentrations give similar results, the following examples merely demonstrate the results over a consistent set of experiments.

The following procedure was used to measure bulk densities. A 100 ml graduated cylinder was cleaned, dried and weighed. The cylinder was filled to the 100 ml level with dried solid. The cylinder was then tapped on a cork pad (to lessen the chance of breakage) a total of ten times. More solid was added to fill back to the 100 ml mark and the cylinder tapped an additional five times. The volume of the solid was then measured and the cylinder was weighed. The bulk density of the solid was calculated from the net weight of solid and the observed volume.

Example 2

Control

Deionized water, 476 g. (26.4 moles), was charged to a reactor purged with a continuous flow of nitrogen and the off gases collected. At ambient temperature, addition of 419 grams of the acrylation intermediates mixture from Example 1 was begun. The moles of water added per mole of dichlorophenylphosphine charged to prepare the 419 g of acrylation intermediate used was 16.5:1. The exothermic nature of the reaction raised the temperature to 85–90° C. as the addition proceeded. Some solids appeared during the reaction which dissolved as the temperature increased. When the addition was completed, the reaction temperature was raised to 90–95° C. and 4–6 grams of 30% hydrogen peroxide were added to destroy any $P_4$ which may have been present from the original dichlorophenylphosphine. The batch was maintained briefly at 90–95° C. and then cooled to about 76° C. where seed crystals were added. After about 10–15 minutes, cooling was resumed until a temperature of 5° C. was reached. The slurry was held at this temperature for 15–30 minutes and then the solid 2-carboxyethyl(phenyl) phosphinic acid was filtered off and washed with a total of 476 grams of cold deionized water. The wet cake was dried and a yield of 323.8 grams of 2-carboxyethyl(phenyl) phosphinic acid or 94.3% was obtained. No hydrogen chloride was removed and collected in this example. The bulk density of the dried solid was 0.504 g/cc.

Example 3

Deionized water, 214 grams (11.89 moles) was charged to a reactor purged with a continuous flow of nitrogen and the off gases collected. At ambient temperature, addition of 419 grams of the acrylation intermediates mixture from Example 1 was begun. The moles of water added per mole of dichlorophenylphosphine charged to prepare the 419 g of acrylation intermediate used was 7.4:1. The exothermic nature of the reaction raised the temperature to 85–90° C. as the addition proceeded. Some solids appeared during the reaction which dissolved as the temperature increased. When the addition was completed, the reaction temperature was raised to 90–95° C. and an additional 262 grams of deionized water (14.56 moles) were added while maintaining temperature. Finally, 4–6 grams of 30% hydrogen peroxide were added to destroy any $P_4$ which may have been present from the original dichlorophenylphosphine. The batch was maintained briefly at 90–95° C. and then cooled to about 76° C. where seed crystals were added. After about 10–15 minutes, cooling is resumed until a temperature of 5° C. is reached. The slurry was held at this temperature for 15–30 minutes and then the solid 2-carboxyethyl(phenyl)-phosphinic acid was filtered off and washed with a total of 476 grams of cold deionized water. The wet cake is dried and a yield of 318.6 grams of 2-carboxyethyl(phenyl)phosphinic acid or 93.% is obtained. In this example 26.0 grams of hydrogen chloride or 22.3% of theory based on dichlorophenylphosphine are collected. The bulk density of the dried solid was 0.573 g/cc.

Example 4

Deionized water, 119 grams (6.61 moles), was charged to a reactor purged with a continuous flow of nitrogen and the off gases collected. At ambient temperature, addition of 419 grams of the acrylation intermediates mixture from Example 1 was begun. The moles of water added per mole of dichlorophenylphosphine charged to prepare the 419 g of acrylation intermediate used was 4.1: 1. The exothermic nature of the reaction raised the temperature to 85–90° C. as the addition proceeded. Some solids appeared during the reaction which dissolved as the temperature increased. When the addition was completed, the reaction temperature was raised to 90–95° C. and an additional 357 grams of deionized water (19.83 moles) were added while maintaining temperature. Finally, 4–6 grams of 30% hydrogen peroxide were added to destroy any $P_4$ which may have been present from the original dichlorophenylphosphine. The batch was maintained briefly at 90–95° C. and then cooled to about 76° C. where seed crystals were added. After about 10–15 minutes, cooling was resumed until a temperature of 5° C. was reached. The slurry was held at this temperature for 15–30 minutes and then the solid 2-carboxyethyl(phenyl) phosphinic acid was filtered off and washed with a total of 476 grams of cold deionized water. The wet cake is dried and a yield of 319.2 grams of 2-carboxyethyl(phenyl)phosphinic acid or 93.2% was obtained. In this example 61.1 grams of hydrogen chloride or 52.4% of theory based on dichlorophenylphosphine were collected. The bulk density of the dried solid was 0.606 g/cc.

Example 5

Deionized water, 58 grams (3.22 moles), was charged to a reactor purged with a continuous flow of nitrogen and the off gases collected. The water was heated to 70–75° C. At this temperature, addition of 419 grams of the acrylation intermediates mixture from Example 1 was begun. The moles of water added per mole of dichlorophenylphosphine charged to prepare the 419 g of acrylation intermediate used was 2.01:1. The exothermic nature of the reaction raised the temperature to 90–95° C. as the addition proceeded. The water was preheated in this example because the solids which appear during the reaction can cause agitation problems until they dissolve as the temperature increases. The reaction can be initiated at ambient if care is taken to allow for the solids. When the addition was complete, the reaction temperature was raised to 125–130° C., held briefly at this temperature, and then an additional 418 grams of deionized water (23.22 moles) were added. The temperature was allowed to lower to 90–95° C. during this addition and was maintained at 90–95° C. until the addition was completed. Finally, 4–6 grams of 30% hydrogen peroxide were added to destroy any $P_4$ which may have been present from the original dichlorophenylphosphine. The batch is maintained briefly at 90–95° C. and then cooled to about 76° C. where seed crystals were added. After about 10–15 minutes, cooling was resumed until a temperature of 5° C. is reached. The slurry was held at this temperature for 15–30 minutes and then the solid 2-carboxyethyl(phenyl)-phosphinic acid was filtered off and washed with a total of 476 grams of cold deionized water. The wet cake was dried and a yield of 318.5 grams of 2-carboxy-ethyl(phenyl)phosphinic acid or 93% is obtained. In this example, 99.5 grams of hydrogen chloride or 85.3% of theory based on dichlorophenylphosphine were collected. The bulk density of the dried solids, was 0.633 g/cc.

Example 6

The procedure followed in Example 4 was repeated except the amount of water charged for the hydrolysis, i.e. the initial water charged to the reactor, and the amount of water added after hydrolysis (calculated as 476 g—grams of water charged for hydrolysis) were varied. The moles of water added per mole of dichlorophenylphosphine charged to prepare the 419 g of acrylation intermediate used was 5.8:1.

Example 7

The procedure followed in Example 5 was repeated except the amount of water charged for the hydrolysis, i.e. the initial water charged to the reactor, and the amount of water added after hydrolysis (calculated as 476 g—grams of water charged for hydrolysis) were varied. The moles of water added per mole of dichlorophenylphosphine charged to prepare the 419 g of acrylation intermediate used was 2.5:1.

Example 8

Comparative

The procedure followed in Example 4 was repeated except the amount of water charged for the hydrolysis, i.e. the initial water charged to the reactor, and the amount of water added after hydrolysis (calculated as 476 g—grams of water charged for hydrolysis) were varied. The moles of water added per mole of dichlorophenylphosphine charged to prepare the 419 g of acrylation intermediate used was 10:1.

The results of Examples 2–8 are reported in Table I.

TABLE I

| Example No. | g $H_2O$ charged | $H_2O$:BPD mole ratio | g HCl removed | % of theoretical HCl removed | bulk density g/cc |
|---|---|---|---|---|---|
| 2 (control) | 476 | 16.5:1 | 0.0 | 0.0 | 0.504 |
| 3 | 214 | 7.4:1 | 26.0 | 22.3 | 0.573 |
| 4 | 119 | 4.1:1 | 61.1 | 52.4 | 0.606 |
| 5 | 58 | 2.01:1 | 99.5 | 85.3 | 0.633 |
| 6 | 166 | 5.8:1 | 43.6 | 37.4 | — |
| 7 | 72 | 2.5:1 | 90.8 | 77.8 | — |
| 8 (comparative) | 288 | 10:1 | 8.0 | 6.9 | — |

In addition, the 2-carboxyethyl(phenyl)phosphinic acid prepared according to the processes of the invention (Examples 3–7) was observed to filter and wash better than the 2-carboxy-ethyl(phenyl)phosphinic acid prepared according to the control (Example 2) or comparative (Example 8) processes.

Examples 9–11

The procedures of Examples 2, 3 and 4 were followed to produce reaction slurries for filtration with the following change in order to maintain a uniform slurry concentration.

Acrylation intermediate (419 g) was added to an appropriate amount of deionized water to give a mole ratio water:acrylate of 4.1:1 (Example 9), 7.4:1 (Example 10) or 16.5:1 (Example 11) as described above. The remaining water was added after the hydrolysis was complete. The change was to add additional water equal to the weight of hydrogen chloride gas collected in a trap during the hydrolysis. This means that in the case of the 4.1:1 hydrolysis, the initial charge to the reactor was 119 g water. Since the "total" water charge is 476 g using the 16.5:1 reaction as a standard in which no hydrogen chloride is collected, the remaining 357 g of water would be added to make the final target slurry concentration of 35 wt %. During the reaction of Example 9, approximately 70 g of hydrogen chloride were collected in a scrubber and since the 35% slurry is based upon weight, the 70 g of HCl was replaced with 70 g water. During the reaction of Example 10, the HCl collected was 38 g., and for the Example 11 there was no HCl collected.

In each case, the liquid reaction mixture was transferred at about 85° C. to a crystallizer programmed to cool the mixture to 15° C. at approximately 0.2° C. per minute. The mixture was seeded at 75° C. during the cooling cycle and the batches were held at 15° C. until filtered.

The filtration procedure used an 0.002 $m^2$ Rosenmund Pocket Filter (Rosenmund Inc.) made of Hastelloy C-22, volume 1000 ml, length 680 mm and diameter 50 mm. The filter medium was a 40 micron polypropylene cloth. The same cloth was used in each study.

The pocket filter was assembled and pressurized with nitrogen to check for leaks. The top was removed and the cold slurry from the crystallizer was added from the top and the unit pressurized with nitrogen to either 14 or 5 psig. When filtration began, the amount of filtrate versus time was recorded, the pressure being kept constant throughout the test. The results of the mother liquor filtrations can be found in FIGS. 1 (14 psig) and 3 (5 psig).

After the cake was considered dewatered, the top of the filter was removed and 476 g of cold (<10° C.) water was added from the top for displacement washing. A portion of this wash water was used to rinse traces of the slurry from the crystallizer into the filter at this time. The top of the filter was replaced and the unit pressurized with nitrogen to either 14 or 5 psig. When filtration began, the amount of filtrate versus time was recorded, the pressure being kept constant throughout the test. When the filtration was complete, the unit was disassembled, the height of the cake in the filter was measured, and the wet filter cake removed. The filter was cleaned and prepared for the next filtration. The results of the wash liquor filtrations can be found in FIGS. 2 (14 psig) and 4 (5 psig).

FIG. 1 demonstrates that the mother liquor filtration rate at 14 psig was better for each of the invention slurries, i.e. the 4.1:1 (Example 9) and 7.4:1 (Example 10) samples, than the control slurry, i.e. the 16.5:1 (Example 11) sample.

Figure 2:
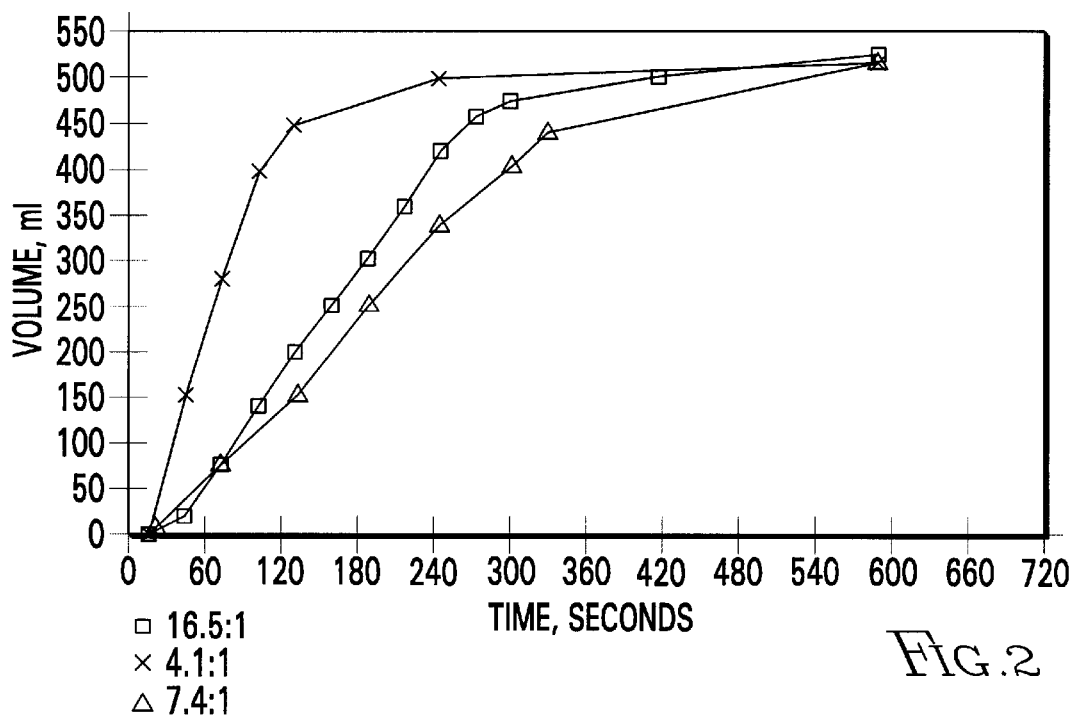
FIG. 2 is a plot of the wash liquid filtration rate at 14 psig filtration pressure.

FIG. 2 demonstrates that the wash filtration rate at 14 psig was substantially better for the 4.1:1 filter cake of the invention than the 16.5:1 control filter cake. The wash filtration of the 7.4:1 filter cake of the invention was slower than the wash filtration of the 16.5:1 control filter cake at 14 psig. The reason that the wash filtration for the 7.4:1 sample is slower than the wash filtration of the 16.5:1 sample is unknown.

Figure 3:
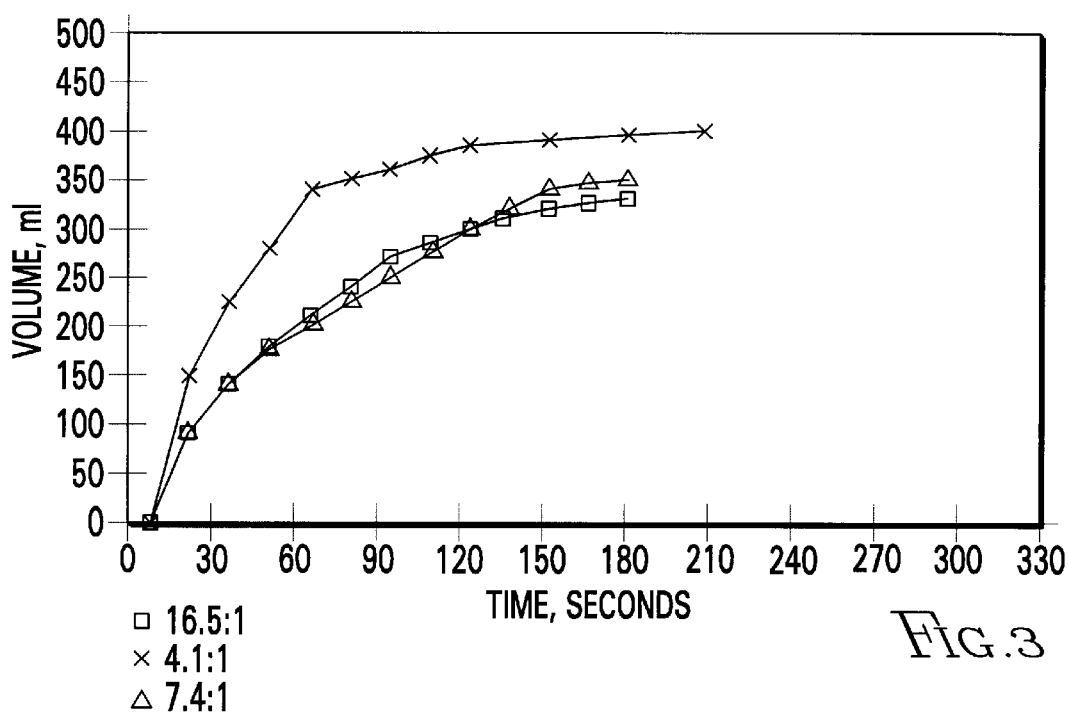
FIG. 3 is a plot of the mother liquor filtration rate at 5 psig filtration pressure.

FIG. 3 demonstrates that the mother liquor filtration rate at 5 psig was substantially better for the 4.1:1 slurry of the invention than the 16.5:1 control slurry. The filtration of the 7.4:1 slurry of the invention was not significantly different than the filtration of the 16.5:1 control slurry at 5 psig. The reason that the mother liquor filtration rates for the 7.4:1 and 16.5:1 samples at 5 psig are not significantly different is unknown.

Figure 4:
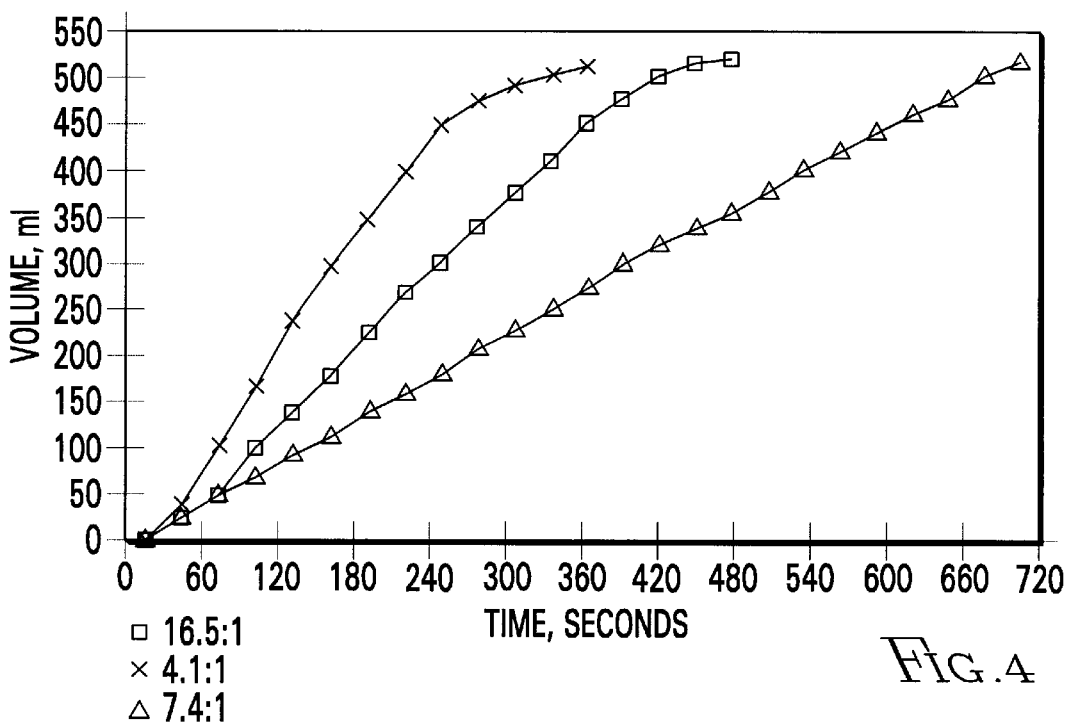
FIG. 4 is a plot of the wash liquid filtration rate at 5 psig filtration pressure.

FIG. 4 demonstrates that the wash filtration rate at 5 psig was better for the 4.1:1 filter cake of the invention than the 16.5:1 control filter cake. The wash filtration of the 7.4:1 filter cake of the invention was slower than the wash filtration of the 16.5:1 control filter cake at 14 psig. The reason that the wash filtration for the 7.4:1 sample is slower than the wash filtration of the 16.5:1 sample is unknown.

Based on the results in Table 1 and the filtration rate data in FIGS. 1–4, it is clear that the processes of the invention produces 2-carboxyalkyl(phenyl)phosphinic acid having improved filterability and product handling (as evidenced by improved filtration rates and increased product bulk density), and improved purity (as evidenced by the removal of HCl).

That which is claimed is:

1. A process for producing 2-carboxyalkyl(phenyl) phosphinic acid comprising:
    (a) admixing water and a first reaction mixture comprising the products of the reaction of dichloro(phenyl) phosphine and a carboxylic acid selected from acrylic acid or methacrylic acid, and
    (b) hydrolyzing said reaction products to produce a second reaction mixture comprising 2-carboxyalkyl (phenyl)phosphinic acid;
wherein the amount of water admixed with said first reaction mixture in step (a) is about 2 to about 7.5 moles water per mole of dichloro(phenyl)phosphine charged to the reaction between dichloro(phenyl)phosphine and carboxylic acid.

2. The process of claim 1 further comprising:
    (c) adding water to said second reaction mixture,
    (d) crystallizing said 2-carboxyalkyl(phenyl)phosphinic acid, and
    (e) recovering said 2-carboxyalkyl(phenyl)phosphinic acid.

3. The process of claim 1 wherein the moles of water per mole of dichloro(phenyl)phosphine charged to the reaction between dichloro(phenyl)phosphine and carboxylic acid is about 2 to about 6.

4. The process of claim 3 wherein the moles of water per mole of dichloro(phenyl)phosphine charged to the reaction between dichloro(phenyl)phosphine and carboxylic acid is 2 to about 4.5.

5. The process of claim 1 wherein said carboxylic acid is acrylic acid and said 2-carboxyalkyl(phenyl)phosphinic acid is 2-carboxyethyl(phenyl)phosphinic acid.

6. The process of claim 5 wherein said reaction products in said first reaction mixture comprise a mixture of 3-(chlorophenylphosphinyl)propionyl chloride, the cyclic anhydride of 2-carboxyethyl(phenyl)phosphinic acid, and the mixed anhydride of acrylic acid with 3-chlorocarbonylethyl(phenyl)phosphinic acid.

7. The process of claim 1 wherein said carboxylic acid is methacrylic acid and said 2-carboxyalkyl(phenyl) phosphinic acid is 2-carboxypropyl(phenyl)-phosphinic acid.

8. The process of claim 7 wherein said reaction products in said first reaction mixture comprise a mixture of 3-(chlorophenylphosphinyl)-2-methylpropanoyl chloride, the cyclic anhydride of 2-carboxypropyl(phenyl)phosphinic acid, and the mixed anhydride of methacrylic acid with 3-chlorocarbonyl-2-methylethyl(phenyl)phosphinic acid.

9. The process of claim 1 wherein HCl gas is removed during the hydrolysis.

10. A process for producing 2-carboxyalkyl(phenyl) phosphinic acid comprising:
    (a) admixing water and a first reaction mixture comprising the products of the reaction of dichloro(phenyl)

phosphine and a carboxylic acid selected form acrylic acid or methacrylic acid, and (b) hydrolyzing said reaction products to produce a second reaction mixture comprising 2-carboxyalkyl (phenyl)phosphinic acid, and simultaneously removing at least a portion of the HCl present during the hydrolysis reaction;

wherein the amount of water admixed with said first reaction mixture in step (a) is the amount effective to enable removal of at least about 20% of the theoretically available chlorine in said first reaction mixture during the hydrolysis.

11. The process of claim 10 further comprising:

(c) adding water to said second reaction mixture, (d) crystallizing said 2-carboxyalkyl(phenyl)phosphinic acid, and (e) recovering said 2-carboxyalkyl(phenyl)phosphinic acid.

12. The process of claim 10 wherein the amount of water admixed with said first reaction mixture in step (a) is the amount effective to enable removal of at least about 35% of the theoretically available chlorine in said first reaction mixture during the hydrolysis.

13. The process of claim 12 wherein the amount of water admixed with said first reaction mixture in step (a) is the amount effective to enable removal of at least about 50% of the theoretically available chlorine in said first reaction mixture during the hydrolysis.

14. The process of claim 10 wherein said carboxylic acid is acrylic acid and said 2-carboxyalkyl(phenyl)phosphinic acid is 2-carboxyethyl(phenyl)phosphinic acid.

15. The process of claim 14 wherein said reaction products in said first reaction mixture comprise a mixture of 3-(chlorophenylphosphinyl)propionyl chloride, the cyclic anhydride of 2-carboxyethyl(phenyl)phosphinic acid, and the mixed anhydride of acrylic acid with 3-chlorocarbonylethyl(phenyl)phosphinic acid.

16. The process of claim 10 wherein said carboxylic acid is methacrylic acid and said 2-carboxyalkyl(phenyl) phosphinic acid is 2-carboxypropyl(phenyl)-phosphinic acid.

17. The process of claim 16 wherein said reaction products in said first reaction mixture comprise a mixture of 3-(chlorophenylphosphinyl)-2-methylpropanoyl chloride, the cyclic anhydride of 2-carboxypropyl(phenyl)phosphinic acid, and the mixed anhydride of methacrylic acid with 3-chlorocarbonyl-2-methylethyl(phenyl)phosphinic acid.

* * * * *